(12) United States Patent
Yamagishi et al.

(10) Patent No.: US 6,370,936 B1
(45) Date of Patent: Apr. 16, 2002

(54) SAMPLING APPARATUS FOR EXHAUST GAS

(75) Inventors: Yutaka Yamagishi; Tetsuji Asami; Shigeru Okuda, all of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/303,794

(22) Filed: Apr. 30, 1999

(30) Foreign Application Priority Data

May 12, 1998 (JP) .......................................... 10-148361

(51) Int. Cl.$^7$ ................................................ G01N 1/00
(52) U.S. Cl. ...................................... 73/1.35; 73/863.03
(58) Field of Search ............................. 73/1.35, 863.23, 73/863.03

(56) References Cited

U.S. PATENT DOCUMENTS 5,072,416 A * 12/1991 Francisco, Jr. et al. ...... 73/1.35
5,243,847 A * 9/1993 Engeljehringer et al.
5,455,781 A * 10/1995 Reynal et al. ............... 73/1.25

* cited by examiner

Primary Examiner—Robert Raevis
(74) Attorney, Agent, or Firm—Oppenheimer Wolff & Donnelly LLP

(57) ABSTRACT

A sampling apparatus for exhaust gas is capable of calibrating two flowmeters each other easily and precisely. A diluting air supply passage for diluting the sampled exhaust gas is connected to an upstream side of a diluting tunnel. A first flowmeter for measuring flow rate of air is provided in the diluting air supply passage. A measuring passage having a filter for capturing particulate matter in the exhaust gas diluted with the diluting air and a second flowmeter for measuring the flow rate of the diluted exhaust gas flowing this filter are connected to a downstream side of the diluting channel. Both flowmeters have high precision. A passage changeover part is provided at the downstream side of the first flowmeter of the diluting air supply passage; a passage changeover part is provided at the upstream side of the second flowmeter in the measuring passage; and a bypass passage is provided between the two passage changeover parts. After calibrating one flowmeter by using a bypass passage, the other flowmeter is calibrated by using the calibrated flowmeter.

1 Claim, 1 Drawing Sheet

SAMPLING APPARATUS FOR EXHAUST GAS

BACKGROUND OF THE INVENTION

1. Field of the Invention

The present invention relates to exhaust gas sampling apparatus used in measuring particulate matter (PM), such as soot and soluble organic fractions (SOF), in exhaust gas for quantitative analysis of PM contained in gas exhausted from diesel engines or the like.

2. Description of the Prior Art

One of the techniques for measuring particulate matter (PM) in exhaust gas conforms to the filter weighing method. In this kind of measurement, for example in the partial dilution method, a sampling apparatus of exhaust gas is used in which part of the exhaust gas is split off and fed into a diluting tunnel as sample gas. This sample gas (exhaust gas) is diluted with air in the dilution tunnel, and the diluted exhaust gas is passed through a filter for capturing PM.

In the partial dilution method, the flow rate of sample gas is determined as the difference of the exhaust gas flow rate after diluting with air and the flow rate of the air used in diluting. Typically, a flowmeter for measuring the flow rate of diluting air and a flowmeter for measuring the flow rate of gas after dilution are provided in the measuring passage and diluting air supply passage, with the difference between respective readings from these flowmeter is determined as the sample gas flow rate.

The two flowmeters must be either calibrated periodically at proper intervals or calibrated, if necessary, before the start of measurement. During calibration, as disclosed, for example, in U.S. Pat. No. 5,243,847, an actual sample gas flow rate (i.e., a differential flow rate) is passed as a calibration gas and is measured by a highly precise flowmeter. A coefficient for correcting the measuring error of flow rate between the two flowmeters is determined, and the two flowmeters are corrected.

However, in the method disclosed in the above-mentioned Patent, it is necessary to pass the actual sample gas as calibration gas, and to determine the coefficient for correcting the measuring error of flow rate between the two flowmeters; hence, the calibration procedure is overly complicated.

SUMMARY OF THE INVENTION

The present invention is devised in the light of the above situation, and it is hence an object to provide a sampling apparatus for exhaust gas that is capable of calibrating two flowmeters easily and precisely, and that is capable of sampling precisely as desired.

To achieve the object, according to the sampling apparatus for exhaust gas of the invention, a diluting air supply passage for diluting a sampled exhaust gas is connected to an upstream side of a diluting tunnel for introducing a portion of air exhaust gas as a sample gas. The diluting air supply passage has a first flowmeter for measuring flow rate of air. A measuring passage having a filter for capturing particulate matter (PM) in the exhaust gas diluted with the diluting air and a second flowmeter for measuring the flow rate of the diluted exhaust gas flowing through this filter are connected to a downstream side of the diluting tunnel. The sample gas flow rate is determined as the difference of the exhaust gas flow rate after dilution and the flow rate of the diluting air, in which both flowmeters are high in precision.

According to another report of the invention, a passage changeover part is provided at the downstream side of the first flowmeter of the diluting air supply passage, and a passage changeover part is provided at the upstream side of the second flowmeter in the measuring passage. A bypass passage is provided between the two passage changeover parts, and beforehand one flowmeter is calibrating by using this bypass passage and another standard flowmeter which is connected to the flowrate check line, the other flowmeter is calibrated by using the calibrated flowmeter as criterion.

The flowmeters used in the sampling apparatus for exhaust gas are preferably flowmeters of high precision, with a flow rate measuring precision of ±0.2% or less, such as Venturi flowmeters.

In the sampling apparatus for exhaust gas of the invention, rather than passing actual sample gas, proper calibration gas is passed into the bypass passage, so that the two flowmeters can be calibrated easily.

DETAILED DESCRIPTION OF THE PREFERRED EMBODIMENT

Figure 1:
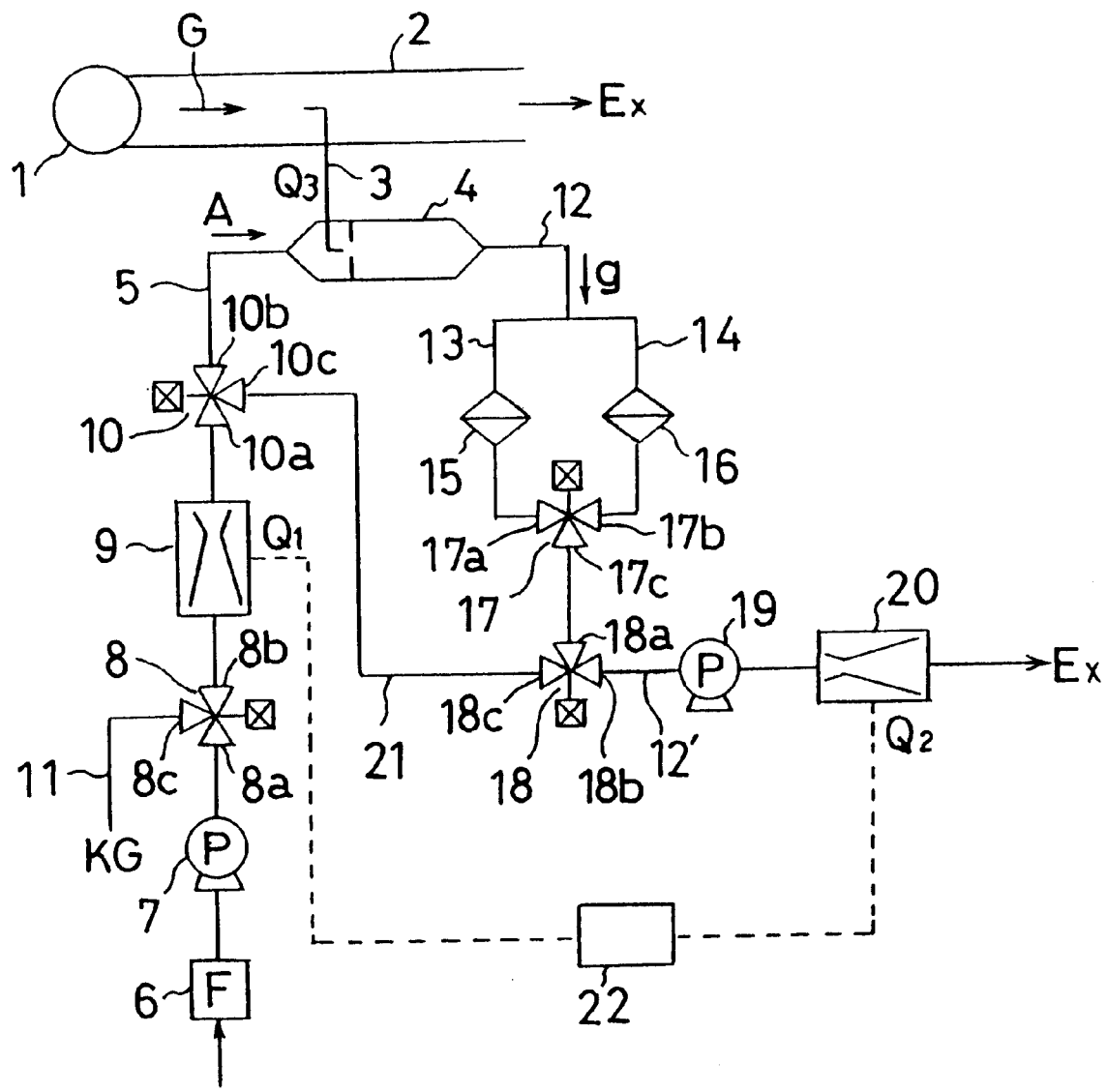
FIG. 1 is a schematic diagram showing an exemplary embodiment of sampling apparatus for exhaust gas of the invention.

A preferred embodiment of the invention is described below while referring to the drawing. FIG. 1 is a diagram schematically showing exemplary sampling apparatus for exhaust gas of the invention. Exemplary apparatus may be used to sample exhaust gas from a diesel engine 1 mounted, for example, on an automobile, with is an exhaust pipe 2 connected thereto. A probe 3 is inserted and connected in the exhaust pipe 2 for sampling a portion of exhaust gas G flowing in the exhaust pipe 2 as sample gas 4 downstream side of the probe 3 is connected to a diluting tunnel 4 for diluting the sampled exhaust gas G.

A diluting air supply passage 5 is connected to the upstream side of the diluting tunnel 4 and supplies air A for diluting the exhaust gas G sampled in the diluting tunnel 4. In the diluting air supply passage 5 are provided in series a filter 6 for taking in air and removing dust and other foreign matter contained therein, a Roots blower pump 7 functioning as 2 suction pump, a three-way solenoid valve 8, a Venturi flowmeter 9 functioning as a first flowmeter for measuring the flow rate of diluting air A, and a three-way solenoid valve 10 functioning as a passage changeover part. A flow rate check line 11 is connected to the three-way solenoid valve 8 and is further connected to, for example, a calibration air tank or standard flowmeter not shown in the drawing. Reference numerals 8a, 8b, 8c are ports of the three-way solenoid valve 8, and reference numerals 10a, 10b, 10c are ports of the three-way solenoid valve 10.

A measuring passage 12 is connected to the downstream side of the diluting tunnel 4 and passes the exhaust gas G diluted with the diluting air A in the diluting tunnel 4. The downstream side of the measuring passage 12 is divided into two passages 13, 14, and the individual passages 13, 14 are provided with filters 15, 16 for capturing particulate matter (PM) contained in the diluted exhaust gas G. Passage 13 is formed as a passage for passing the exhaust gas when measuring particulate matter (PM), and passage 14 is formed as a passage for passing exhaust gas while not measuring PM.

A three-way solenoid valve 17 functions as a passage changeover means provided at the downstream side of the measuring passage 13 and bypass passage 14. A port 17a of valve 17 is connected to passage 13, a port 17b to passage 14, and a port 17c to passage 14 at the downstream side of the three-way solenoid valve 13.

In measuring passage 12', a three-way solenoid valve 18 functioning as a passage changeover part, a Roots blower pump 19 functioning as a suction pump, and a Venturi flowmeter 20 functioning as a second flowmeter for measuring the flow rate of the diluted exhaust gas S are provided sequentially from its upstream side in this order. The downstream side of passage 12' is, for example, an exhaust.

Reference numeral 21 indicates a passage for bypassing the diluting tunnel 4 and filters 15, 16, connected between the three-way solenoid valve 10 provided at the downstream side of the first flowmeter 9 in the diluting air supply passage 5 and the three-way valve 18 provided between the filter of the measuring passage 12' and the suction pump 19.

A control operation unit 22 composed of, for example, a microcomputer, turns on and off the suction pumps 7, 19, controls the opening and closing of the three-way solenoid valves 8, 10, 17, 18, and receives the detection outputs from the flowmeters 9, 20.

The operation of the sampling apparatus for exhaust gas, is described below. In PM measurement, measuring particulate matter (PM) by supplying the diluting air A into the diluting tunnel 4 through the three-way solenoid Valve 8, the first flowmeter 9, and the three-way solenoid valve 10, the exhaust gas G flowing in the exhaust pipe 2 is sampled into the diluting tunnel 4. The sampled exhaust gas G is diluted with the diluting air A in the diluting tunnel 4, and the diluted exhaust gas G flows in the measuring passage 12. This diluted exhaust gas G flows in passage 13 when measuring PM, and any PM is captured by the filter 15. The diluted exhaust gas G passing through the filter 15 is exhausted through the three-way solenoid valves 17, 18, suction pump 19, and second flowmeter 20.

In this case, the flow rate $Q_3$ of the exhaust gas sampled in the diluting tunnel 4 (the exhaust gas before dilution, that is, the sample gas) is defined as follows, assuming the detected flow rates by the first flowmeter 9 and second flowmeter 20 to be $Q_1$ and $Q_2$, respectively.

$$Q_3 = Q_2 - Q_1$$

Incidentally, the flow rate precision $\Delta Q/Q$ of the Venturi flowmeter alone used as the first flowmeter 9 and second flowmeter 20 is approximately expressed in the following simplified formula:

$$\Delta Q/Q = \tfrac{1}{2} \times (\Delta T/T + \Delta dP/dP - \Delta P/P)$$

where T, P, and dP are outputs of temperature sensor, differential pressure sensor, and pressure sensor (not shown) provided near the Venturi flowmeter.

The flow rate precision $\Delta Q_3/Q_3$ of the flow rate of difference between the Venturi flowmeters 9, 20 is as follows when neither flowmeter 9 nor flowmeter 20 is calibrated or when calibrated without relating to each other:

$$\Delta Q_3/Q_3 = \sqrt{[(\Delta Q_2/Q_2)^2 - (\Delta Q_1/Q_1)^2]}$$

The flow rate precision $\Delta Q_3/Q_3$ is, therefore, expressed by the square mean of the Venturi flowmeters 9, 20. However, when the flow rate is calibrated by relating to each other, it follows that:

$$\Delta Q_3/Q_3 = \Delta Q_2/Q_2 - \Delta Q_1/Q_1$$

Accordingly, in the sampling apparatus for exhaust gas of the invention, the Venturi flowmeters 9, 20 are calibrated as follows.

First, a calibrated standard Venturi flowmeter (not shown) is connected to the flow rate check line 11; the three-way solenoid valve 8 is changed over; calibration air KG is passed into the flow rate check line 11; and the Venturi flowmeter 9 is calibrated as the first flowmeter on the basis of the flow rate in the standard Venturi flowmeter.

Next, by changing over the three-way valves 10, 18, the Venturi flowmeter 9 as the first flowmeter and the Venturi flowmeter 20 as the second flowmeter are connected mutually in series through the passage 5, three-way solenoid valve 10, bypass passage 21, three-way solenoid valve 18, and passage 12'. In this state, the calibration air KG is passed in from the flow rate check line 11, and the flow rate of the Venturi flowmeter 20 is calibrated on the basis of the flow rate of the previously calibrated Venturi flowmeter 9.

Thus, in the sampling apparatus for exhaust gas of the invention, without passing actual sample gas (exhaust gas), the two flowmeters 9, 20 can be calibrated easily by only passing a proper calibration gas, such as calibration air, into the bypass passage 21.

Moreover, the Venturi flowmeters used as the two flowmeters 9, 20 are capable of measuring at high precision, e.g., with a flow rate measuring precision of ±0.2% or less. In addition, unlike mass flowmeters, Venturi flowmeters do not contain flow rate detecting mechanism by capillaries, which have a large effect on airtight density that is likely to fall in trouble, so that it is possible to measure the flow rate stably at high precision and for a long period. Therefore, the sampling apparatus for exhaust gas thus calibrated can sample desired gasp stably for a long period.

Furthering the explanation herein by presenting numerical values, in the actual flow rate range ($Q_2$: 75 liters/min to 130 liters/min), the precision of a single flowmeter is ±0.1% full scale to ±0.2% full scale. Therefore, for example, if the flow rate of the difference is 30 liters/min, the flow rate error of the difference is ±0.28% full scale at maximum when the Venturi flowmeters 9, 20 are not calibrated with each other. And if the Venturi flowmeters 9, 20 are calibrated with each other, the flow rate error is ±0.2% full scale at maximum.

In the sampling apparatus for exhaust gas in the embodiment described above, the precision of the flow rate is the product of the actual difference flow rate multiplied by the diluting ratio $q[=Q_1/(Q_2-Q_1)]$. Therefore, when the difference flow rate $Q_3$ is 30 liters/min, supposing $Q_2$=130 liters/min, $Q_1$=95 liters/min, at q=3.7, we obtain ±0.2(=±0.06× 3.7)% full scale.

When the diluting ratio q is large, for example, q=40 ($Q_2$=130 liters/min, $Q_1$=127 liters/min), since the flow rates are nearly the same in the two flowmeters 9, 20, the error of the two flowmeters 9, 20 can be minimized by mutual calibration. And supposing the independent precision of the flowmeters 9, 20 is ±0.1%, we obtain an error of ±4.0(= ±0.1×40)% full scale.

Incidentally, when the flow rate difference at the span point of the two flowmeters 9, 20 is zero, by calibrating so that the error may be zero, the error becomes smaller when the diluting ratio q is greater.

The invention is not limited to this embodiment alone, but, for example, the second flowmeter 20 may be calibrated first, and the first flowmeter 9 may be calibrated on the basis of this calibrated second flowmeter 20. Moreover, the measuring passage 12 connected to the downstream side of the diluting tunnel 4 may be branched in three or more divisions on the way, and a filter may be provided in each divided passage. Alternatively, the passage may be only one up to the three-way solenoid valve 18, and a filter may be provided in this single passage.

In the sampling apparatus for exhaust gas of the invention, two flowmeters can be calibrated each other very easily and precisely, and desired sampling may be done stably and precisely for a long period of time.

What is claimed is:

1. An apparatus for sampling exhaust gas, said apparatus comprising:
    a diluting tunnel having an upstream side and a downstream side, said diluting tunnel for receiving exhaust gas as a sample gas;
    a diluting air supply passage connected to said upstream side of said diluting tunnel, said diluting air supply passage for providing diluting air to said diluting tunnel to dilute said exhaust gas, said downstream side of said diluting tunnel thereby having diluted exhaust gas;
    a first flowmeter disposed in said diluting air supply passage, said first flowmeter for measuring a flow rate of said diluting air flowing in said diluting air supply passage;
    a measuring passage connected to said downstream side of said diluting tunnel, said measuring passage for receiving said diluted exhaust gas;
    a filter disposed in said measuring passage, said filter for capturing particulate matter in said diluted exhaust gas;
    a passage changeover part disposed downstream of said first flowmeter on said diluting air supply passage;
    a second flowmeter disposed in said measuring passage, said second flowmeter for measuring a flow rate of said diluted exhaust gas flowing in said measuring passage;
    a passage changeover part disposed downstream of said second flowmeter on said measuring passage;
    a bypass passage provided between said passage changeover parts; and a sample gas flow rate being the difference of said flow rate of said diluted exhaust gas and said flow rate of said diluting air.

* * * * *